United States Patent
Walsh et al.

(10) Patent No.: US 6,200,265 B1
(45) Date of Patent: Mar. 13, 2001

(54) PERIPHERAL MEMORY PATCH AND ACCESS METHOD FOR USE WITH AN IMPLANTABLE MEDICAL DEVICE

(75) Inventors: Kevin K. Walsh, Peoria, AZ (US); David L. Thompson, Fridley, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/293,699

(22) Filed: Apr. 16, 1999

(51) Int. Cl.$^7$ ................................................. A61B 5/00
(52) U.S. Cl. ............................................ 600/300; 128/903
(58) Field of Search ...................... 600/300, 301, 600/309, 325, 327, 339, 341; 128/903; 607/119, 116, 149, 48

(56) References Cited

U.S. PATENT DOCUMENTS

| | | |
|---|---|---|
| 4,375,817 | 3/1983 | Engle et al. . |
| 4,379,459 | 4/1983 | Stein . |
| 4,384,585 | 5/1983 | Zipes . |
| 4,440,173 | 4/1984 | Hudziak et al. . |
| 4,476,868 | 10/1984 | Thompson . |
| 4,494,950 * | 1/1985 | Fischell ................... 128/903 |
| 4,548,209 | 10/1985 | Wielders et al. . |
| 4,556,063 | 12/1985 | Thompson et al. . |
| 4,577,633 | 3/1986 | Berkovits et al. . |
| 4,587,970 | 5/1986 | Holley et al. . |
| 4,622,979 | 11/1986 | Katchis et al. . |
| 4,693,253 | 9/1987 | Adams et al. . |
| 4,726,380 | 2/1988 | Vollmann et al. . |
| 4,821,723 | 4/1989 | Baker et al. . |
| 4,830,006 | 5/1989 | Haluska et al. . |
| 4,880,005 | 11/1989 | Pless et al. . |
| 4,949,719 | 8/1990 | Pless et al. . |
| 4,949,730 | 8/1990 | Cobben et al. . |
| 4,987,897 | 1/1991 | Funke . |
| 5,113,859 | 5/1992 | Funke . |
| 5,113,869 | 5/1992 | Nappholz et al. . |
| 5,131,388 | 7/1992 | Pless . |
| 5,144,949 | 9/1992 | Olson . |
| 5,158,078 | 10/1992 | Bennett et al. . |
| 5,188,105 | 2/1993 | Keimel . |
| 5,191,891 | 3/1993 | Righter . |
| 5,199,428 | 4/1993 | Obel et al. . |
| 5,207,218 | 5/1993 | Carpentier et al. . |
| 5,289,824 | 3/1994 | Mills et al. . |
| 5,292,343 | 3/1994 | Blanchette et al. . |
| 5,311,396 | 5/1994 | Steffen . |
| 5,312,446 | 5/1994 | Holschbach et al. . |
| 5,312,453 | 5/1994 | Shelton et al. . |

(List continued on next page.)

*Primary Examiner*—Eric F. Winakur
(74) *Attorney, Agent, or Firm*—Thomas F. Woods; Harold R. Patton; Girma Wolde-Michael

(57) ABSTRACT

A peripheral memory patch apparatus for attachment to a patient's skin includes a high capacity memory for storing physiologic data uplinked from an implantable medical device. A resilient substrate provides support for a memory, microprocessor, receiver, and other electronic components. The substrate flexes in a complimentary manner in response to a patient's body movements. The substrate is affixed to the patient's skin with the use of an adhesive which provides for comfort and wearability. The low profile peripheral patch apparatus is preferably similar in size and shape to a standard bandage, and may be attached to the patient's skin in an inconspicuous location. A status indicator provides for a visual, verbal, or tactile indication of the operational status of the peripheral memory patch. Uplinking of physiologic telemetry data from the internal memory of an implantable medical device to the peripheral memory patch is initiated in response to a transfer signal produced by the peripheral memory patch. The transfer signal may be generated by the implantable medical device or upon actuation of a switch by the patient. Various telemetry techniques including radio frequency, acoustic, and body bus telemetry techniques, may be employed to transfer information between the implantable medical device and the peripheral memory patch.

55 Claims, 7 Drawing Sheets

U.S. PATENT DOCUMENTS

| | | |
|---|---|---|
| 5,314,430 | 5/1994 | Bardy . |
| 5,330,507 | 7/1994 | Schwartz . |
| 5,331,966 | 7/1994 | Bennet et al. . |
| 5,336,245 | 8/1994 | Adams . |
| 5,354,316 | 10/1994 | Keimel . |
| 5,447,519 | 9/1995 | Peterson . |
| 5,480,842 | 1/1996 | Clifton et al. . |
| 5,489,624 | 2/1996 | Kantner et al. . |
| 5,511,553 | 4/1996 | Segalowitz . |
| 5,534,018 | 7/1996 | Wahlstrand et al. . |
| 5,536,768 | 7/1996 | Kantner et al. . |
| 5,545,186 | 8/1996 | Olson et al. . |
| 5,634,468 | 6/1997 | Platt et al. . |
| 5,683,432 | 11/1997 | Goedeke . |
| 5,759,199 | 6/1998 | Snell et al. . |
| 5,891,180 | 4/1999 | Greeninger et al. . |
| 5,948,006 * | 9/1999 | Mann .................................. 128/903 |

* cited by examiner

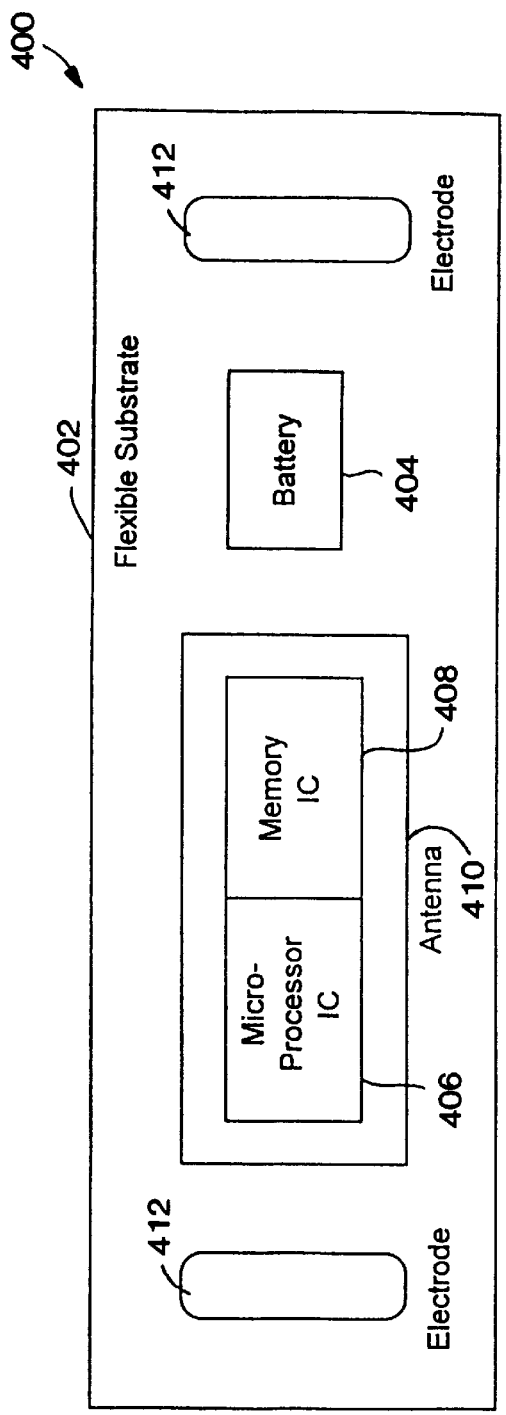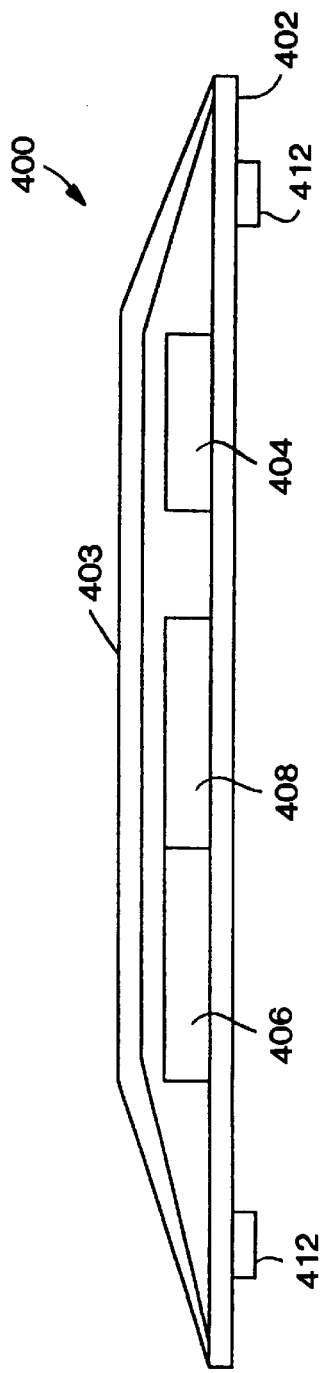
FIG. 6
FIG. 7

PERIPHERAL MEMORY PATCH AND ACCESS METHOD FOR USE WITH AN IMPLANTABLE MEDICAL DEVICE

FIELD OF THE INVENTION

The present invention relates generally to physiologic data acquisition and storage in an implantable medical device. More particularly, the present invention pertains to a peripheral memory apparatus for attachment on a patient's skin that cooperates with an internal memory of an implantable medical device to provide for an expanded data storage capability.

BACKGROUND OF THE INVENTION

Various medical devices have been developed that acquire information from one or more physiologic sensors or transducers. A typical physiologic sensor transduces a measurable parameter of the human body, such as blood pressure, temperature, or oxygen saturation, for example, into corresponding electrical signals. In many implantable medical device applications, it is often desirable or necessary to acquire physiologic data for extended periods of time and on a continuous basis. Moreover, in many applications, it is often desirable or necessary to provide for such extended periods of physiologic data acquisition through use of an apparatus that is both convenient for the patient to use and one which does not draw public attention to the patient's condition. It is well understood that conspicuous or easily noticed medical devices and equipment often provide a disincentive for patients to participate in needed testing, evaluation, and therapies.

A problem well known to designers of implantable medical devices, such as pacemakers, for example, concerns the necessity to use low power components, including low power memory components, within the implantable medical device. Use of low power components is considered necessary in order to provided for extended periods of implantable electronic device operation and to reduce the need to repeatedly replace batteries which can only be accomplished through surgical means. As a consequence, conventional implantable medical devices typically employ low voltage, low current memory devices which have limited storage capacity and access speed, and often lag behind the state-of-the-art in memory technology by several years. These and other limitations significantly decrease the data storage and access capability of implantable medical devices, and often precludes the opportunity to integrate high capacity, low cost, state-of-the-art memory devices in implantable medical device designs.

Various implementations of portable or user-worn electrocardiographic recording/monitoring devices are known in the art, examples of which may be found in the issued U.S. Patents listed in Table 1 below.

TABLE 1

| Patent No. | Inventor(s) | Issue Date |
| --- | --- | --- |
| 5,759,199 | Snell et al. | Jun. 2, 1998 |
| 5,634,468 | Platt et al. | Jun. 3, 1997 |
| 5,511,553 | Segalowitz | Apr. 30, 1996 |
| 5,289,824 | Mills et al. | Mar. 1, 1994 |
| 5,191,891 | Righter | Mar. 9, 1993 |
| 5,113,869 | Nappholz et al. | May 19, 1992 |
| 4,622,979 | Katchis et al. | Nov. 18, 1986 |

The patents listed in Table 1 hereinabove are hereby incorporated by reference herein in their respective entireties. As those of ordinary skill in the art will appreciate readily upon reading the Summary of the Invention, the Detailed Description of Various Embodiments, and the Claims set forth below, many of the devices and methods disclosed in the patents identified below and listed above in Table 1 may be modified advantageously by using the teachings of the present invention.

A conventional portable or user-worn electrocardiographic (ECG) monitor/recorder, such as those disclosed in one or more of the patents listed in Table 1 above, typically requires an external harness to secure the device to a patient during use. Moreover, such conventional ECG monitoring devices are generally conspicuous and readily perceivable by others, and must typically be removed prior to exposure to water or other hostile environments. As was previously described hereinabove, an important and often necessary requirement for providing effective testing and evaluation is ensuring that the monitoring device will be worn by the patient during the entirety of the testing period.

An ECG monitoring/recording device which is conspicuous to onlookers creates a disincentive to wear such devices. Such conventional ECG monitoring devices must also be removed during bathing or swimming, thus interrupting the acquisition of data during these times. Also, conventional ECG monitoring/recording devices are limited in terms of their ability to acquire only electrocardiographic data obtained through contact with the patient's skin.

SUMMARY OF THE INVENTION

The present invention has certain objects. That is, various embodiments of the present invention provide solutions to one or more problems existing in the prior art with respect to the acquisition and storage of physiologic data, particularly physiologic data acquired by an implantable medical device (IMD). Such problems associated with prior art implantable medical device storage approaches include, for example, a limited capacity for storing physiologic and other data, particularly physiologic data acquired on a continuous basis over an extended period of time; the inability to exploit state-of-the-art, high capacity/high speed, low-cost memory technologies; a dependency on sophisticated uplink and data storage systems for extracting physiologic data acquired by an implantable medical device; and the inconvenience associated with requiring a patient to visit a physician location to facilitate uplinking of IMD data on a repeated basis in order to prevent saturation of the IMD memory and possible loss of physiologic data due to IMD memory saturation.

Various embodiments of the present invention have the object of solving at least one of the foregoing problems. While some systems have been able to solve the general problem of storing limited amounts of physiologic data in an implantable medical device, such approaches have generally resulted in implementations that require frequent uplinking of acquired physiologic data to expensive receiving/storing systems and requiring patients to make frequent visits to a physician's office to extract physiologic data stored in the implantable medical device. It is therefore another object of the present invention to provide an improved apparatus and methodology for acquiring and storing physiologic, diagnostic, and other data acquired by an implantable medical device that fulfills at least one of the foregoing objects.

In comparison to known implementations of implantable medical device storage devices, various embodiments of the present invention may provide one or more of the following advantages: providing expanded memory resources for the purpose of storing physiologic and other data acquired or produced by an implantable medical device, providing for the continuous storage of physiologic data acquired by an implantable medical device over an extended period of time, such as on the order of days, increasing the ease by which large amounts of physiologic data may be acquired, providing a comfortable and inconspicuous apparatus for effectively extending the memory capacity of an implantable medical device, eliminating the need for a patient to make repeated visits to a physician's office for the sole purpose of extracting physiologic data stored in an implantable medical device, downloading patch programs which are programmed into IMD random access memory (RAM) to allow functional changes to the implanted device for problem patients, to test and evaluate algorithms, to gather data for research activities, and the like, and allowing all or nearly all of the RAM memory to be used for downloadable patches, with the diagnostic data being stored in the peripheral memory patch.

Some embodiments of the invention include one or more of the following features: a peripheral memory patch apparatus for attachment to a patient's skin which includes a high capacity memory for storing physiologic data uplinked from an implantable medical device; a resilient substrate that provides support for memory and other electronic components which flexes in a complimentary manner in response to a patient's body movements; a packaging configuration that is affixed to the patient's skin with the use of an adhesive which provides for increased comfort and wearability; a low profile packaging configuration similar in size and shape to a standard bandage which may be attached to the patient's skin in an inconspicuous and non-perceivable location; a status indicator which provides for a visual, audible, verbal, or tactile indication of the operational status of the peripheral memory patch; a capability to initiate uplinking of physiologic telemetry data from the internal memory of an implantable medical device to the peripheral memory patch in response to a transfer signal produced by the peripheral memory patch, the implantable medical device, or upon actuation of a switch by the patient; and use of various telemetry techniques including radio frequency, acoustic, and body bus telemetry techniques.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6 shows various electrical, electronic, and structural elements of a peripheral memory patch from a top view perspective in accordance with an embodiment of the present invention; and FIG. 7 shows the peripheral memory patch of FIG. 6 from a cross-sectional view perspective.

Figure 1:
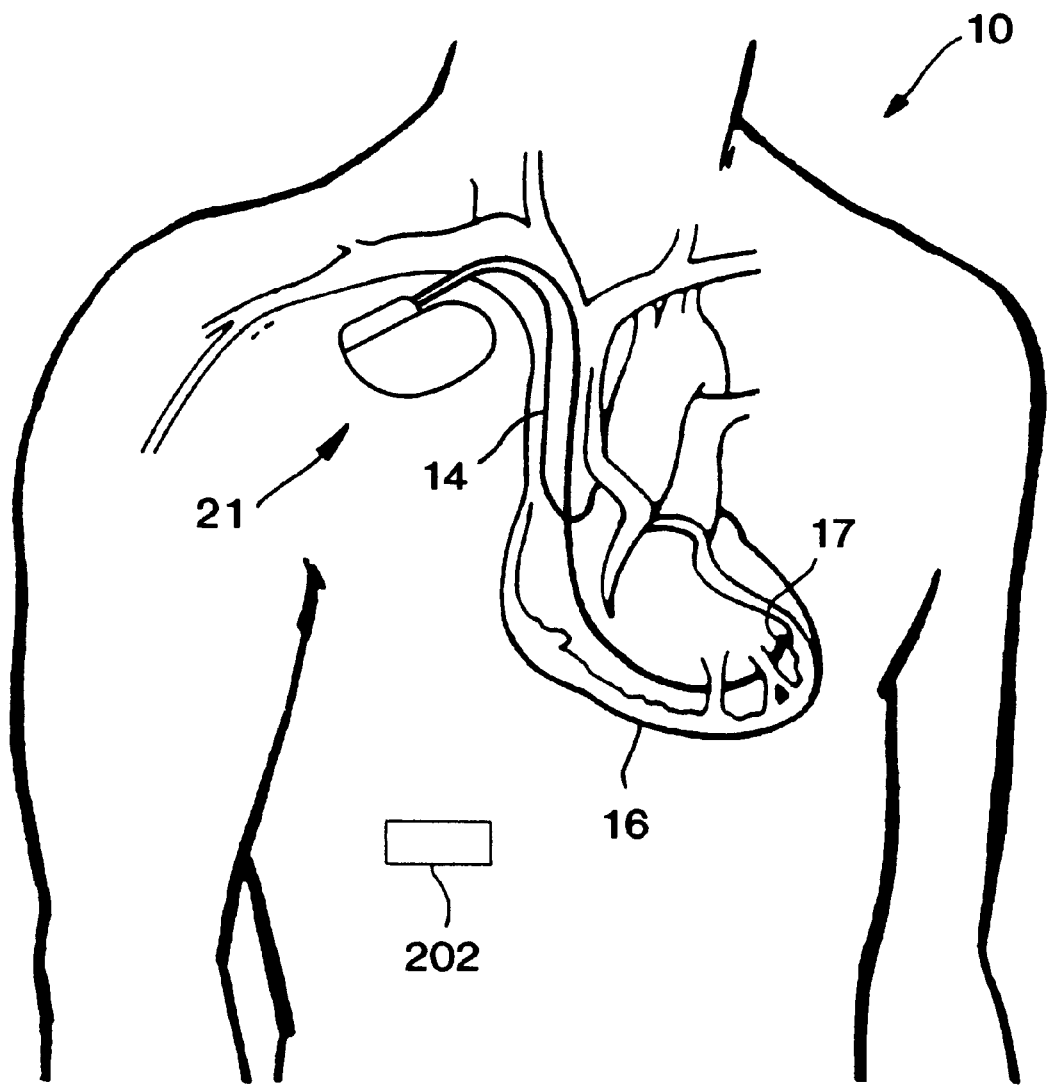
FIG. 1 shows an implantable medical device implanted in a human body that communicates physiologic, diagnostic, and other information to a peripheral memory patch in accordance with an embodiment of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. A variety of implantable medical devices are described or referred to herein that cooperate with a peripheral memory patch attached on a patient's skin so as to define various system embodiments of the present invention that provide for the communication of physiologic, diagnostic, and other information between the subject implantable medical device and the peripheral memory patch. A number of peripheral memory patch embodiments are also described herein. It is to be understood that other embodiments may be utilized, and structural and functional changes may be made without departing from the scope of the present invention.

FIG. 1 is a simplified schematic view of a medical device 21 implanted in a human body 10. Implantable medical device 21 represents one of a wide variety of implantable electrical devices that may be readily adapted to cooperatively operate with a peripheral memory patch of the present invention. A transducer assembly 17 is shown implanted in a human heart 16 and coupled to medical device 21. The transducer assembly 17 includes a lead 14 to which one or more sensors are attached, each of which senses one or more physiologic parameters associated with the human heart 16. A peripheral memory patch 12, which cooperates with implantable medical device 21 in accordance with the principles of the present invention to greatly expand the memory resources of device 21, is shown affixed to a patient's skin.

In the case where the implanted medical device 21 shown in FIG. 1 is a pacemaker, a conductor of lead 14 is typically connected between the heart 16 and implantable medical device 21. An electrode attached to lead 14 senses electrical signals attendant to the depolarization and re-polarization of the heart 16 and transmits pacing pulses for causing depolarization of cardiac tissue in the vicinity of the distal ends thereof. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described below. A peripheral memory patch of the present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

Alternatively, medical device 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as the Medtronic chronicle as substantially described in U.S. Pat. No. 5,331,966 issued to Bennet et al., all of which are hereby incorporated herein by reference in their respective entireties. The implantable monitoring device may monitor any of the following parameters; oxygen, pressure, cardiac flow, stroke volume, cardiac acceleration, etc. The present invention is believed to find wide application to any form of implantable electrical device which requires storage of appreciable amounts of physiologic, diagnostic, system, or other data, particularly those that acquire such information on a continuous or near continuous basis.

In general, the implantable medical device 21 shown in FIG. 1 includes a hermetically-sealed enclosure that may include various elements, such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, in addition to other elements. The telemetry transceiver antenna and circuit may further transmit stored data in a telemetry uplink to a peripheral memory patch of the present invention.

Figure 2A:
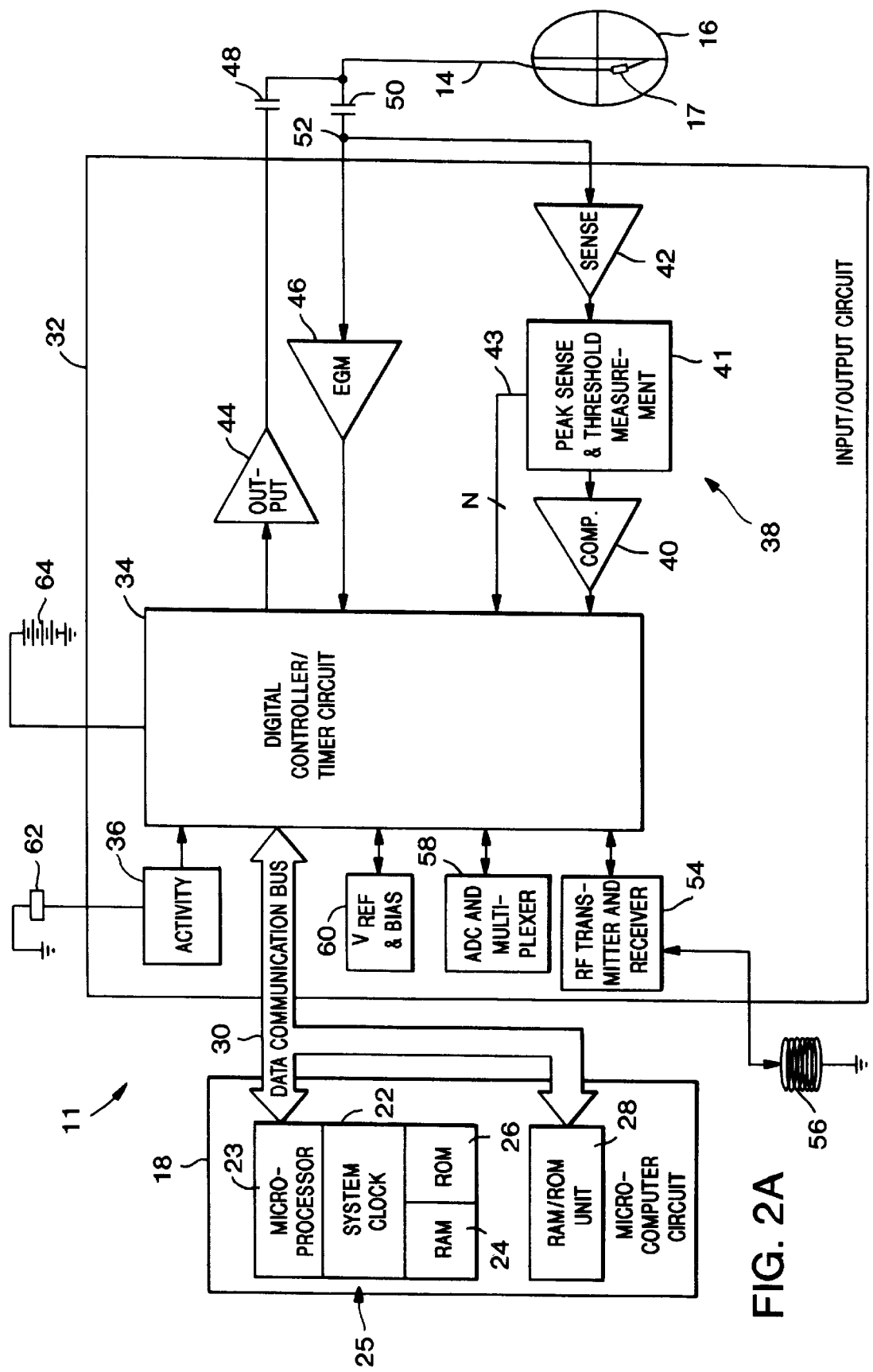
FIG. 2A shows an implantable pacemaker device that communicates physiologic, diagnostic, and other information to a peripheral memory patch in accordance with one embodiment of the present invention.

FIG. 2A is a block diagram illustrating various components of a pacemaker 11 which represents one of many implantable medical devices that may advantageously cooperate with a peripheral memory patch in accordance with the present invention. In one embodiment, the pacemaker 11 is programmable by means of an external programming unit (not shown). One such programmer suitable for the purposes of the present invention is the commercially available Medtronic Model 9790 programmer. The programmer is a microprocessor device which provides a series of encoded signals to pacemaker 11 by means of a programming head which transmits radio frequency (RF) encoded signals to pacemaker 11 according to a telemetry system such as that described in U.S. Pat. No. 5,292,343 to Blanchette et al., incorporated by reference herein in its entirety.

It is to be understood, however, that the programming methodology disclosed in the Blanchette et al. patent is identified herein for illustrative purposes only and that any programming methodology may be employed so long as the desired information is transmitted to and from the pacemaker 11. One of skill in the art may choose from any of a number of available programming techniques to accomplish this task.

Pacemaker 11, illustratively shown in FIG. 2A, is electrically coupled to the patient's heart 16 by lead 14. Lead 14, which may include one or multiple conductors, is coupled to a node 52 in the circuitry of pacemaker 11 through input capacitor 50. In the presently disclosed embodiment, an activity sensor 62 provides a sensor output to a processing/amplifying activity circuit 36 of input/output circuit 32. Input/output circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 20, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34.

The electrical components shown in FIG. 2A are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. For example, data acquired and stored in pacemaker 11 may be transmitted via RF transmitter and receiver unit 54 to a peripheral memory patch in accordance with the principles of the present invention. Unit 54 may correspond to the telemetry and program logic disclosed in U.S. Pat. No. 4,556,063 issued to Thompson et al., hereby incorporated by reference herein in its entirety, or to that disclosed in the above-referenced Blanchette et al. patent.

Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by a peripheral memory patch of the present invention or an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patients heart 16 through coupling capacitor 48 in response to a pacing trigger signal provided by digital controller/timer circuit 34. For example, each time the escape interval times out or an externally transmitted pacing command is received, a trigger is initiated as is well known in pacing art. Output amplifier 44, for example, may correspond generally to the output amplifier disclosed in U.S. Pat. No. 4,476,868 to Thompson, also incorporated by reference herein in its entirety.

Figure 2B:
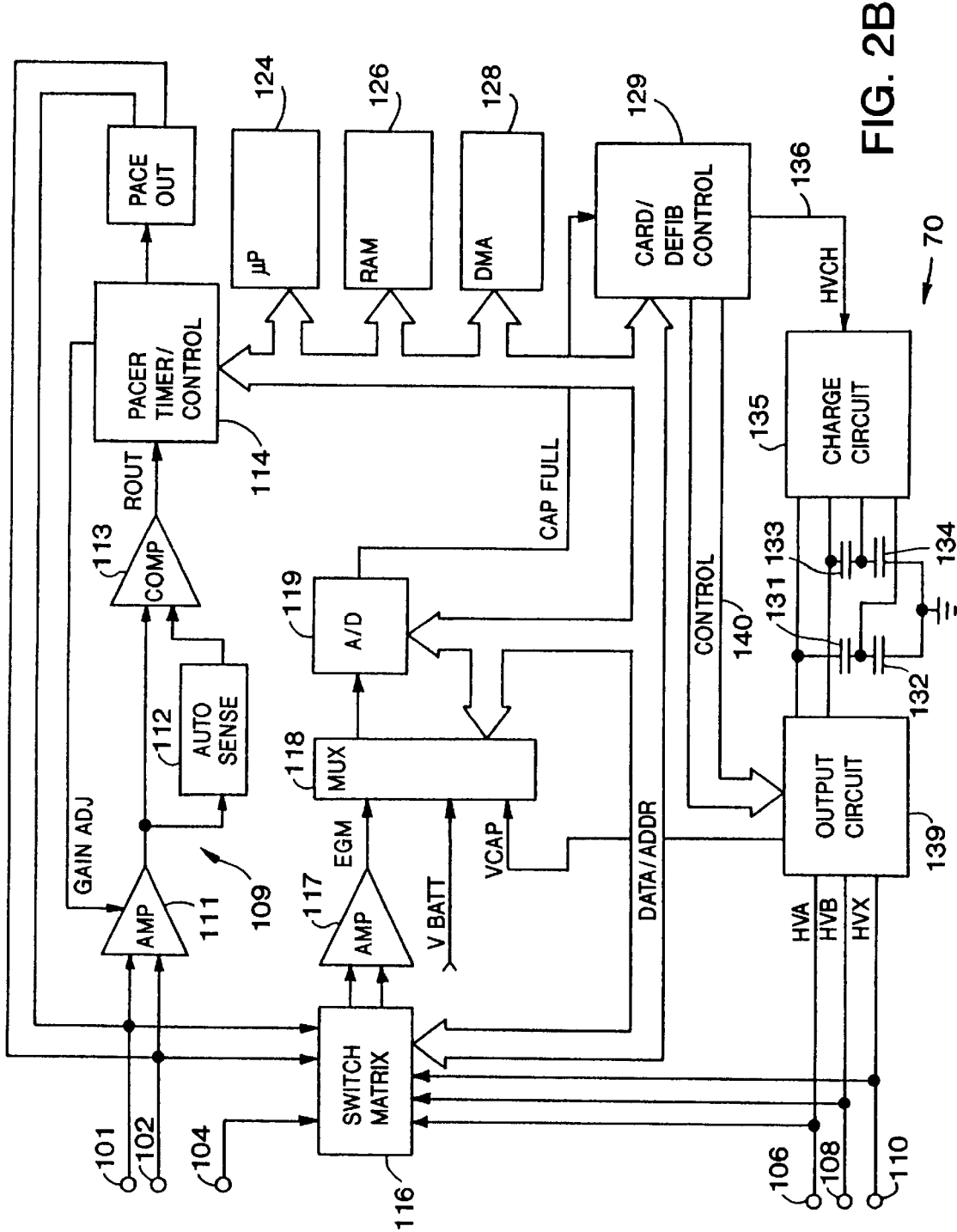
FIG. 2B shows one illustrative embodiment of a pacemaker/cardioverter/defibrillator unit that communicates physiologic, diagnostic, and other information to a peripheral memory patch in accordance with another embodiment of the present invention.

FIG. 2B is a functional schematic diagram from U.S. Pat. No. 5,447,519 to Peterson which shows an implantable pacemaker/cardioverter/defibrillator (PCD) 70 which represents another one of many implantable medical devices that may cooperate with a peripheral memory patch of the present invention to communicate physiologic, diagnostic, and other data from PCD 70 to the peripheral memory patch for storage therein. U.S. Pat. No. 5,447,519 is incorporated by reference herein in its entirety. It is understood that this diagram is an illustration of an exemplary type of device in which the invention may find application, and is not intended to limit the scope of the present invention. For example, the present invention is also believed to be useful in conjunction with implantable PCDs as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/fibrillation discrimination function. Far field EGM signals from the selected electrodes are passed through band pass amplifier 117 and into multiplexer 118, where they are converted to multi-bit digital data signals by A/D converter 119 for storage in random access memory 126 under the control of direct memory address circuitry 128.

The processor 124 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 70 of FIG. 2B is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,375,817 to Engle et al., all of which are incorporated herein by reference in their respective entireties. Further, known circuitry for controlling the timing and generation of anti-tachycardia pacing pulses is described in U.S. Pat. No. 4,577,633 to Berkovitz et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Many implantable medical devices, such as those disclosed herein, are designed to acquire and store physiologic data which is periodically transferred to an external receiving system typically situated at a physician's office or other health care facility. In some applications, it is considered important or critical that physiologic data be acquired and stored on a continuous basis over many hours, such as 24 to 48 hours for example. It can be appreciated that the present state of memory technology suitable for utilization in implantable medical devices severely limits the data storing capacity of such devices. In view of present data storage capacity limitations, a patient equipped with an implantable medical device must make repeated and often extended visits to a physician's office or other health care facility to ensure that meaningful physiologic data is captured and not lost due to the saturation of the implantable medical device's memory resources.

It will be appreciated that a peripheral memory patch apparatus and methodology according to the present invention may be implemented in a wide variety of implantable medical devices and is not limited to application in the devices described or referred to herein. The present invention is believed to find wide application to any form of implantable electrical device that acquires physiologic data from a patient which is subsequently or contemporaneously transmitted to a data storage device situated external to the patient. The present invention is believed to be particularly advantageous in those applications where physiologic data storage resources provided within an implantable medical device or other implantable electrical device are limited.

Figure 3:
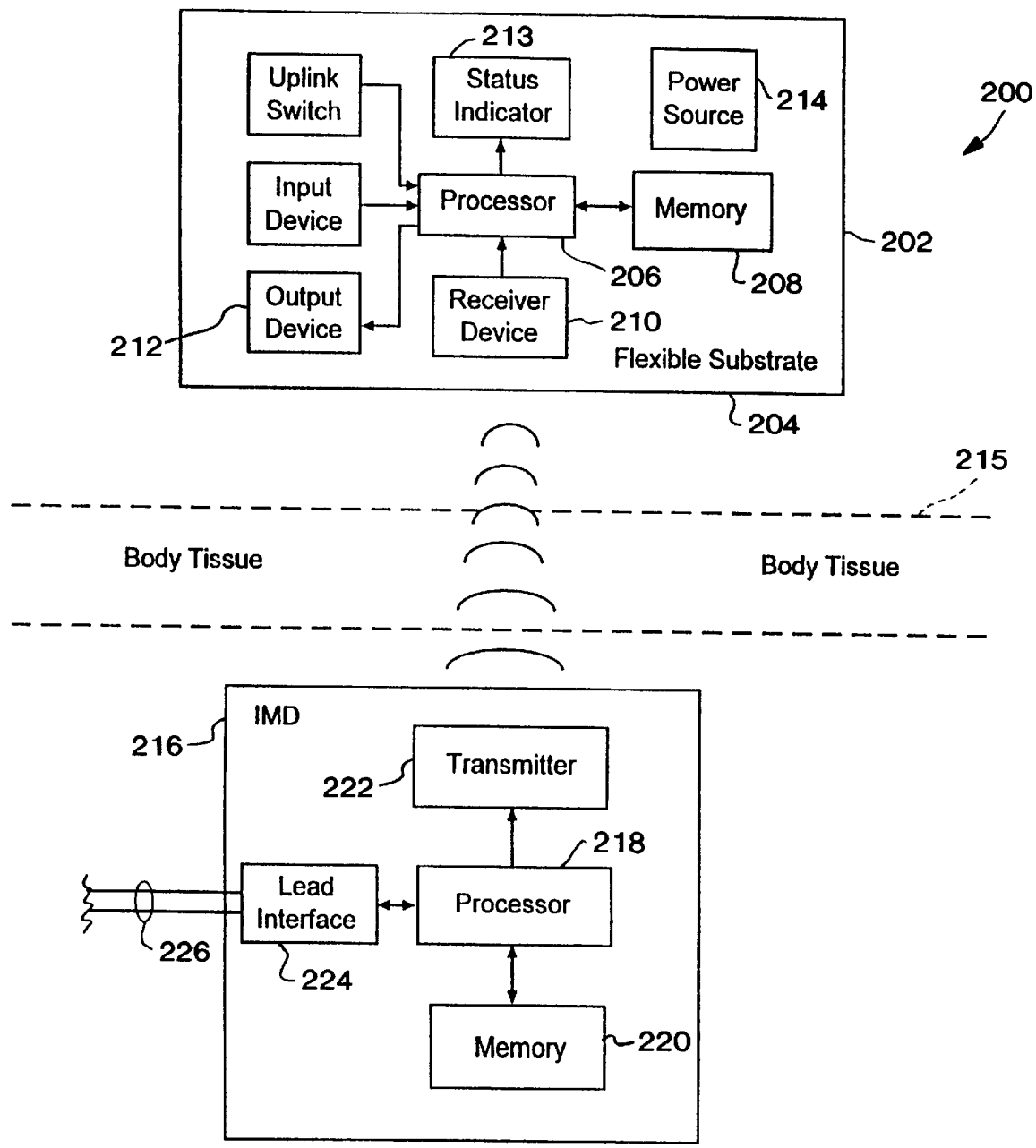
FIG. 3 shows a system block diagram of a peripheral memory patch apparatus operating cooperatively with an implantable medical device in accordance with an embodiment of the present invention.

FIG. 3 shows a block diagram illustrating various components of a system 200 for acquiring and storing physiologic data of a patient in accordance with an embodiment of the present invention. The system 200 includes a peripheral memory patch 202 and an implantable medical device 216. The implantable medical device 216 includes a processor 218 which is coupled to a memory 220. The processor 218 is further coupled to a transmitter 222 and to a lead interface 224. The lead interface 224 is coupled to a lead 226 which communicates various sensed signals produced by one or more physiologic sensors (not shown) connected to the distal end of lead 226. It is understood that implantable medical device 216 is representative of one of a variety of implantable electrical devices, such as one of the devices referred to herein.

In general operation, implantable medical device 216 acquires physiologic, diagnostic, and other data which is stored in memory 220. As was discussed previously in the Background, memory 220 is representative of a low voltage, low current, low capacity memory which is typically employed in an implantable medical device, and is limited in terms of storage capacity and access speed due to power and size constraints. As such, memory 220 is typically limited in terms of total storage space allocated for the purpose of storing physiologic and other diagnostic data.

A peripheral memory patch 202 of the present invention effectively extends the memory capacity of an implantable medical device 216 by providing additional memory resources which may be utilized by implantable medical device 216. The embodiment of a peripheral memory patch 202 shown in FIG. 3 is constructed on a flexible substrate 204 and provided with an adhesive (not shown) such that the peripheral memory patch 202 may be directly applied to the skin of a patient at a desired location. Peripheral memory patch 202 includes a processor 206 which is coupled to a receiver device 210, memory 208, and output device 212, respectively. A power source 214, also disposed on flexible substrate 204, provides power to the active components of peripheral memory patch 202. In one embodiment, peripheral memory patch 202 is packaged in a size and form similar to that of a commercially available adhesive bandage.

Figure 4:
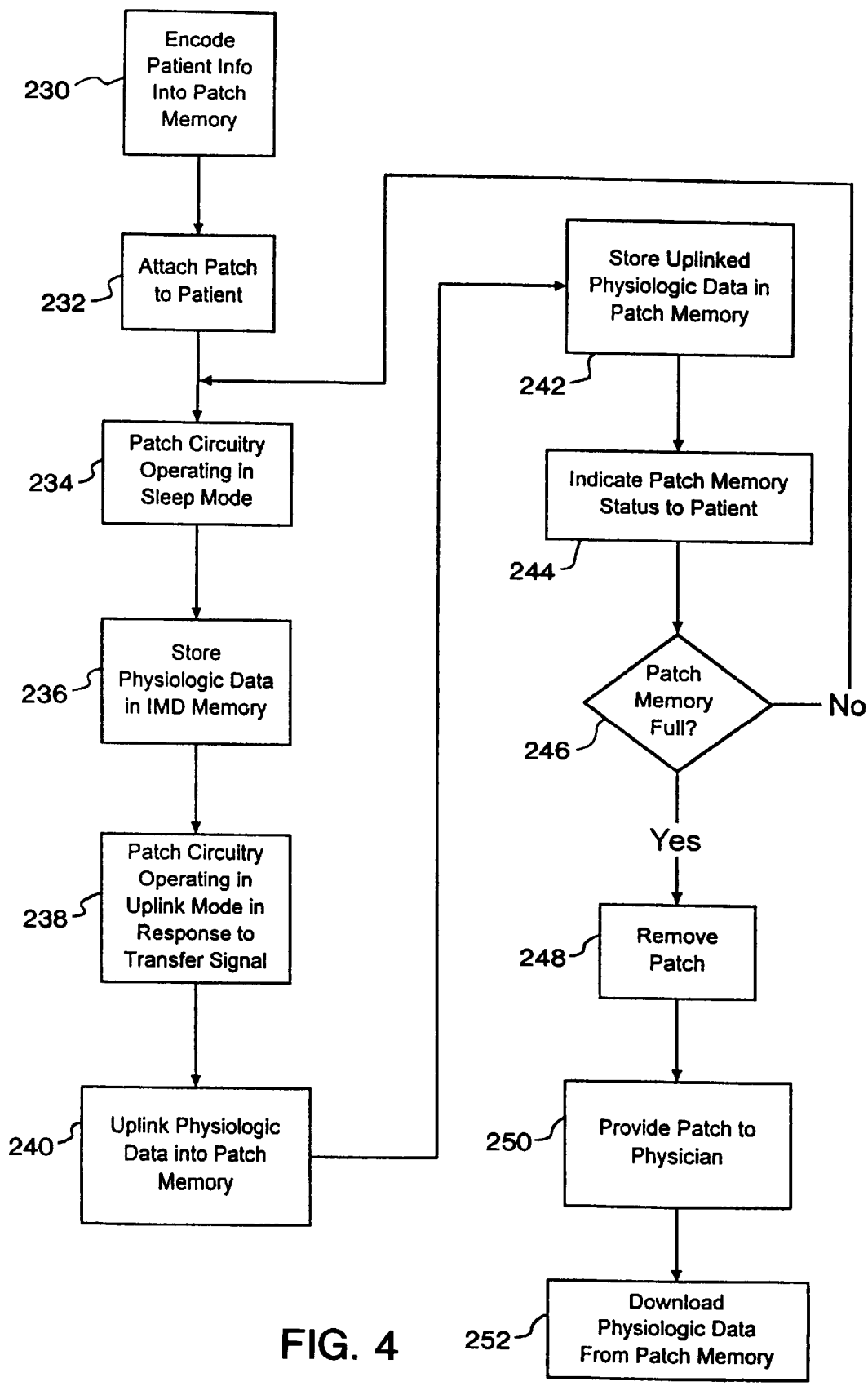
FIG. 4 shows a flow diagram which describes various process steps associated with the operation of a peripheral memory patch in accordance with an embodiment of the present invention.

In general operation, and as further shown in FIG. 4, information concerning the patient is initially encoded into memory 208 of peripheral memory module 202 prior to use, typically at a physician's office. An input device or interface (not shown) is typically employed to facilitate encoding 230 of patient information into memory 208. It is understood that this input device may be provided by replacing output device 212 with a suitable input/output interface. After encoding patient information into memory 208, peripheral memory patch 202 is attached 232 to the patient. Peripheral memory patch 202 includes an adhesive for affixing the patch 202 to the skin of the patient.

Initially, the circuitry of peripheral memory patch 202 may operate 234 in a sleep mode for purposes of conserving power. Upon attachment to the patient, a periodic impedance measurement will detect the impedance change (i.e., from infinity to several thousand ohms or less) and turn on the peripheral memory patch 202. The impedance measurement may be implemented as described in U.S. Pat. No. 5,534,018 to Wahlstrand, et al., which is incorporated herein by reference in its entirety. While operating in sleep mode, implantable medical device 216 acquires physiologic data and stores such data in memory 220 in accordance with its programming. In response to a transfer signal received by receiver device 210 of peripheral memory patch 202 or in response to a transfer signal generated within peripheral memory patch 202, the patch circuitry transitions from a sleep mode to an uplink mode of operation. While operating in an uplink mode, physiologic data stored in memory 220 of implantable medical device 216 is transmitted 240 to receiver device 210 of peripheral memory patch 202. The received physiologic data is then transferred to memory 208 for storage therein. Following completion of an data uplink operation, the circuitry of peripheral memory patch 202 may again transition to a sleep mode of operation until such time as another transfer signal is generated or received 242.

An important aspect of the present invention concerns the capacity of memory 208 provided on peripheral memory patch 202. In general, memory 208 has a storage capacity many times greater than that of memory 220 of implantable medical device 216. As such, memory 208 of peripheral memory patch 202 may accept physiologic and other data uplinked from memory 220 of IMD 216 over an extended period of time prior to memory 208 of peripheral memory patch 202 reaching full capacity. As such, IMD 216 effectively utilizes memory 208 of peripheral memory patch 202 as an extended or expanded memory, thus permitting IMD memory 208 to continuously store newly received data over an extended duration of time without threat of memory saturation.

Peripheral memory patch 202 may include an indicator that provides a patient with an indication 244 of the status of memory 208. Peripheral memory patch 202, by way of example, may be provided with a tactile transducer that provides mild stimulation to the patient's skin proximate patch 202 as an indication that memory 208 is nearing zero capacity. Alternatively, a visual or audible indicator may be provided on peripheral memory patch 202 to provide a patient with a visual or audible indication of patch memory status and/or operating condition. If memory 208 is full or nearing zero capacity 246, peripheral memory patch 202 may be removed from the skin by the patient 248 and subsequently provided to a physician 250 or other healthcare provider. It is contemplated that peripheral memory patch 202 may be inserted into a standard mailing envelope and forwarded to the physician via regular mail.

Upon receiving peripheral memory patch 202, personnel at a physician's office or healthcare clinic may download 252 physiologic and other data, such as medical device diagnostic information, stored in memory 208 of peripheral memory patch 202. In one embodiment, peripheral memory patch 202 is intended to be discarded after one use. Alternatively, the electronics module section of peripheral memory patch 202 may be reused following an appropriate cleaning procedure and provided with a new adhesive tape or layer for subsequent or repeated use. It is noted that the power source 214, which may be a low profile battery, may be replaced to allow continued reuse of peripheral memory module 202.

Figure 5:
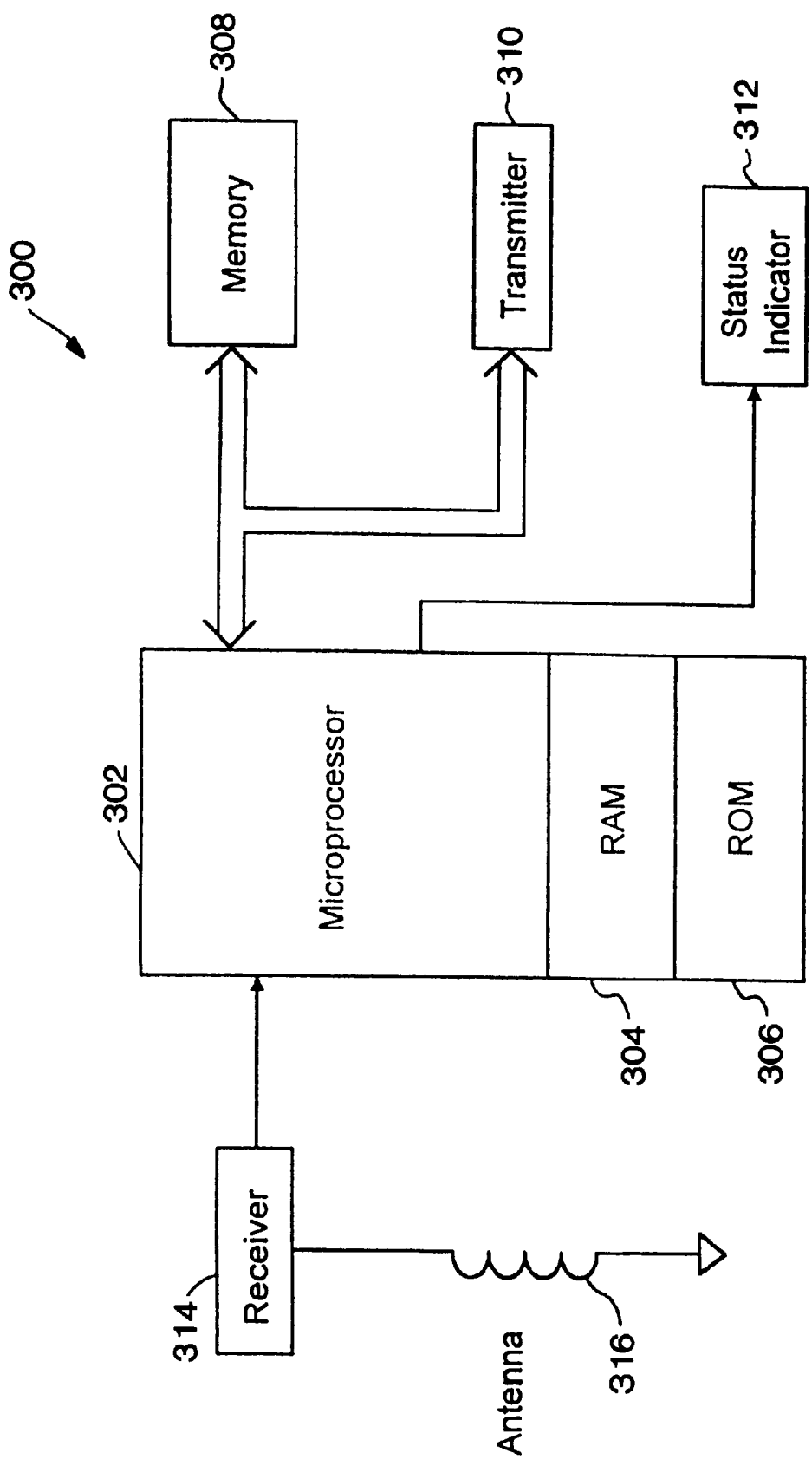
FIG. 5 shows a system block diagram of the electronics module of a peripheral memory patch in accordance with an embodiment of the present invention.

FIG. 5 shows a system block diagram of various components of a peripheral memory patch 300 in accordance with an embodiment of the present invention. In accordance with the embodiment shown in FIG. 5, peripheral memory patch 300 includes a microprocessor 302 coupled to system random access memory (RAM) 304 and system read-only-memory (ROM) 306. Microprocessor 302 is also coupled to a memory 308 which, in accordance with a system view, operates as an extended memory with respect to the internal memory of an implantable medical device with which peripheral memory patch 300 communicates.

Peripheral memory patch 300 further includes a receiver 314 which is coupled to an antenna 316. Antenna 316 and receiver 314 cooperate to receive a telemetry signal transmitted by an implantable medical device using any of a variety of telemetry techniques. A transmitter 310 provides for downloading of physiologic, diagnostic, and other information stored in memory 308 of peripheral memory patch 300. A status indicator 312 provides a tactile, visual or audible indication of patch memory status and/or operating condition to the patient.

FIGS. 6 and 7 respectively show top and side cross-sectional views of a peripheral memory module in accordance with another embodiment of the present invention. A peripheral memory patch 400, in accordance with the embodiment depicted in FIGS. 6 and 7, is provided on a flexible substrate 402. Substrate 402 includes an adhesive backing (not shown) which provides for both comfort and extended periods of wear when affixed directly on the patient's skin.

It is contemplated that peripheral memory patch 400 may be attached to a patient's skin for periods of about one to two days. Although extended periods of wear on the order of one to two weeks may be desirable or necessary under certain circumstances, it is known that such long-term continuous contact between the adhesive and skin can result in minor itching problems. In an alternative embodiment, substrate 402 may flexible or rigid, and may be provided with a hook and loop type of securing arrangement to affix peripheral memory patch 400 to a piece of clothing worn by the patient. In this embodiment, it is assumed that the telemetry technique utilized, such as certain RF and body bus telemetry approaches, allows for wide separation distances between the transmitter of the implantable medical device and the antenna 410 of peripheral memory patch 400.

Flexible substrate 402 may include hydrophilic pressure sensitive adhesives and conductive gels and, in addition, may have a construction similar to that disclosed in U.S. Pat. Nos. 5,489,624 and 5,536,768, both of which are hereby incorporated by reference herein in their respective entireties. Flexible substrate 402 may have a size and shape similar to that of commercially available disposable bandages. In one embodiment, flexible substrate 402 has a width dimension ranging between approximately 0.5" and approximately 3", and a length dimension ranging between approximately ¾" and approximately 5". Peripheral memory patch 400 may have a thickness dimension ranging between approximately 0.025" and approximately 0.25".

In the embodiment illustrated in FIGS. 6 and 7, flexible substrate 402 may comprise a resilient material upon which several electronic and electrical components are mounted. Flexible substrate 402 may include an integral or separate interconnect pattern of electrical conductors that provide for interconnection between the various components disposed on flexible substrate 402. Suitable materials that may be used to fabricated flexible substrate 402 include mylar, flexible foil, flex PC, Kapton, and polymer thick film (PTF).

The electronic portion of peripheral memory patch 400 includes a microprocessor integrated circuit (IC) 406 and a memory IC 408. Shown surrounding microprocessor 406 and memory 408 is an antenna 410 which receives uplinked physiologic data transmitted by an implantable medical device, such as IMD 216 shown in FIG. 3. Also provided on flexible substrate 402 is a battery 404 and one or more electrodes 412. In one embodiment, flexible substrate 402 and the various components populating flexible substrate 402 which define the electronics module of peripheral memory patch 400 are fabricated and packaged in accordance with various known "smart card" technologies, examples of which are disclosed in U.S. Pat. Nos. 5,311,396 and 5,480,842, both of which are incorporated herein by reference in their respective entireties.

The electronics module of peripheral memory patch 400 may include a flexible foil substrate 402 with an attached battery 404 and chip-on-board (COB) memory chips 408. In accordance with one embodiment, battery 404 may have a lithium manganese oxide (e.g., $LiMnO_2$) chemistry, and may be of a sealed foil design. Although a rectangular shape to the various components is shown in FIGS. 6 and 7, various other component geometries, such as square, round or oval shapes, may be employed.

Memory 408 may constitute a single memory IC or several memory ICs. Memory 408 is preferably a state-of-the-art, commercially-available memory which may be embodied in various memory technologies (e.g., CMOS). Memory 408, for example, may include one or more dynamic random access memories (DRAMs), static random access memories (SRAMs), electrically erasable programmable read-only memories (EEPROMs), flash memories, ferroelectric memories, and/or analog memories.

As was discussed previously in the Background, and with reference to FIG. 3, memory 220 of a typical IMD 216 must typically exhibit low voltage and low current characteristics which are required attributes for a memory device used in an implantable medical device. It is understood that the power requirements of peripheral memory patch 400 may be significantly more liberal than those associated with internal memories 220 of implantable medical devices. In contrast to an internal memories 220 of an implantable medical device, memory 408 of a peripheral memory patch 400, as is shown in FIGS. 6 and 7, may exploit higher voltage/current memory devices, including various commercial grade devices, which offer high storage capacities and access speeds at an appreciably lower cost as compared to memories 220 used within implantable medical devices 216. By way of example, memory 408 of peripheral memory patch 400 may be configured using 128 megabyte (Mb) DRAMs or 128 Mb flash memories in contrast to a 32 kilobyte (Kb)×8 SRAMs or 256 kb×8 SRAMs which are suitable for use as internal memories 220 of implantable medical devices 216.

Further examples of suitable DRAMs which are commercially-available and may be employed in peripheral memory patch 400 include models MT48LC2M8A1 (16 Mb), MT48LC8MA82 (64 Mb), and MT48LC16M8A2 (128 Mb), all of which are manufactured by Micron Corporation. An example of a suitable analog memory which may be employed in peripheral memory patch 400 is described in U.S. Pat. No. 5,312,446, which is incorporated herein by reference in its entirety.

Referring again to FIG. 3, and in accordance with another embodiment of the present invention, provision of memory 208 in peripheral memory patch 200 provides the opportunity to utilize internal memory 220 in IMD 216, which is typically a RAM memory, in a variety of unconventional ways. By way of example, memory 208 of peripheral patch 200 may be used as a primary storage location for physiologic and other data acquired or produced by IMD 216, while memory 220 of IMD 216 operates as a buffer during the time the acquired physiologic data is transmitted to memory patch 200 and stored in memory 208.

In this regard, a first portion of memory 220 is allocated, such as by partitioning memory 220, for short-term storage of physiologic data acquired by IMD 216. This first portion of memory 220 cooperates with memory 208 of peripheral memory patch 200 to provide for an expanded memory capacity for purposes of storing physiologic, diagnostic, system, and other data over and above the capacity provided by IMD memory 220.

A second portion of IMD memory 220 may be used for storing downloadable program code in the form of program changes, "patches," diagnostic programs, and other programs and algorithms that may be downlinked from a programmer or other external interactive remote monitoring and/or telemetry device. By way of example, the second portion of IMD memory 220 may store downloaded evaluation program code which provides for specialized testing, evaluation, and data gathering for a particular patient. The results of such an evaluation may be stored in the first portion of IMD memory 220 and subsequently uplinked to an external programming or monitoring/telemetry device. A physician may then analyze the evaluation results and, if needed, prescribe a modification to the functional programming of IMD 216.

It will be appreciated that effectively expanding the internal memory 220 of IMD 216 via external memory 208 of peripheral memory patch 202 provides for the opportunity to significantly reduce the size of internal IMD memory 220, such as to a size needed only for buffering physiologic data acquired by IMD 216. Decreasing the size of internal IMD memory 220 may further provide for an appreciable reduction in IMD power consumption and, therefore, a significantly longer in-patient service life.

It will be further appreciated that cooperative operation between peripheral memory patch 202 and IMD 216 provides for a number of other advantages, including increased ease of use, reduced cost of the IMD 216, an improved capability of testing IMD 216 and the patient's physiologic wellbeing, reduced costs associated with monitoring problem or high risk patients, such as those experiencing tachyarrhythmia and heart failure, with automatic and/or patient initiated physiologic data capture, and the ability to integrate into the peripheral memory circuitry a memory device or devices that are considered state-of-the-art.

In addition, another advantage realized through employment of a peripheral memory patch in accordance with the present invention concerns the capability to provide one day, two day, or several days of continuous patient monitoring through cooperative storing of acquired physiologic data between memory 220 of IMD 216 and memory 208 of peripheral memory patch 200. Another advantage concerns the ability to provide continuous, long-term recording of physiologic information without the use of an ambulatory belt-worn ECG recorder or holter device.

Further, an expanded data storing capability provided by employment of peripheral memory patch 200 concerns the ability to effectively monitor dislodgment of a lead coupled to IMD 216, such as a pacing lead. This may be used to allow the pacemaker implant to be performed on an outpatient implant basis (i.e., no overnight stay). An example of lead dislodgment monitoring is disclosed in U.S. Ser. No. 08/966,107, entitled "Pacing Lead Impedance Monitoring Circuit for Non-Physiologic Sensing," filed Nov. 7, 1997, which is hereby incorporated herein by reference in its entirety.

Initially, physician loaded patient data, such as patient name, identification number, date/time of monitoring initiation, physician name, and contact phone number, for example, may be entered into the memory 208 to allow for proper tracking and following of acquired and stored patient data. In accordance with one embodiment, the internal memory 220 of IMD 216 stores ambulatory data (e.g., atrial and/or ventricular IEGM, markers, diagnostic counters, sensor data, etc.) until a pre-established capacity threshold has been reached, such as a near memory full threshold for example. The ambulatory data stored in memory 220 of IMD 216 may then be uplinked to memory 208 of peripheral memory patch 200 in the form of data blocks or other streamed data configuration.

Alternatively, internal memory 220 of IMD 216 may be partitioned to permit approximately 50% to 90% of the internal memory space to be filled and subsequently transmitted to peripheral memory patch 200 while permitting storage of acquired physiologic data in the remaining portion of the internal memory space. The manner and magnitude of partitioning of internal IMD memory 220 may be based on various factors, including memory size, the speed of uplinked telemetry, the rate at which physiologic data is acquired by IMD 216, and other considerations. It is understood that percentages of memory partitioning described above is provided for illustrative purposes only and not of limitation.

Peripheral memory patch 200 preferably operates in a sleep mode or a powered down mode until required to be activated in order to receive a block of data from IMD 216. Activation may be effected via a wake-up transmission received from IMD 216 prior to data uplink or, alternatively, via synchronized clocking allowing for activation at a predetermined time. Further, telemetry may involve situating peripheral memory patch 200 in close proximity above IMD 216 in accordance with the telemetry techniques disclosed in previously referenced U.S. Pat. No. 4,556,063 to Thompson. A further alternative telemetry approach may involve placing peripheral memory patch 200 over a pacing lead 14 and establishing a telemetry link as described in U.S. Pat. No. 4,440,173 to Hudziak et al.

Yet another alternative approach permits peripheral memory patch 200 to be located anywhere on the patients body when a radio frequency telemetry approach as described in U.S. Pat. No. 5,683,432 to Goedeke or a body bus telemetry approach is employed, such as those disclosed in U.S. Pat. No. 4,987,897 and 5,113,859 to Funke, all of which are hereby incorporated herein by reference in their respective entireties. Another suitable body bus telemetry approach is disclosed in U.S. Ser. No. 09/218,946, entitled "Telemetry for implantable devices using the body as an antenna," to Ryan and filed on Dec. 22, 1998, which is hereby incorporated herein by reference in its entirety.

Referring again to the system embodiment shown in FIG. 5, microprocessor 302 may be a low cost PIC microcontroller from Microchip Technology. In one embodiment, the components shown in FIG. 5, other than memory 308, may be implemented as an application specific integrated circuit (ASIC) using either an on-board microprocessor or a random logic design implementation.

Status indicator 312 shown in FIG. 5 provides for patient feedback as to the status of peripheral memory patch 200, such as an indication of the remaining storage capacity of memory 308 for receiving additional uplinked physiologic data. Status indicator 312 may include one or more light emitting diodes (LEDs), a liquid crystal display (LCD) or a verbal messaging device, such as one which includes an audio signal processor (e.g., ISD ChipCorder as described in U.S. Pat. No. 5,891,180, which is hereby incorporated herein by reference in its entirety). The integration of intracardiac electrogram (IEGM) and/or sensor analog data and marker data may be accomplished consistent with the methodologies employed in U.S. Pat. No. 5,312,446.

Status indicator 312 may also include a tactile indicator, such as a low level subcutaneous stimulation device. In the embodiment illustrated in FIGS. 6 and 7, two electrodes 412 define a tactile status indicator which produces low level subcutaneous stimulation via the pair of electrodes 412 so as to cause a mild twitch or tingling sensation. Status indicator 312 thus provides for feedback, indications, and warning information concerning the proper or improper functioning of peripheral memory patch 200, such as "memory filled" status.

The memory of a peripheral memory patch in accordance with the principles of the present invention may have a capacity of approximately 44 Mb, which provides for approximately 24 hours of recording of one channel of information when no compression methodology is employed and a sampling rate of approximately 512 Hertz (Hz) is assumed. Various known data compression techniques may be employed to reduce the memory size requirements of a peripheral memory patch of the present invention.

For example, a turning point compression algorithm, such as that described in U.S. Pat. No. 5,312,446, may be employed to provide for 24 hours of continuous recording of one channel of information at a 512 Hz sampling rate, which requires only 11 Mb of memory. In a three channel system, such as one that provides for recording of atrial, ventricular IEGM, and sensor data (e.g., activity sensor, pressure sensor, oxygen saturation sensor, stroke volume sensor, cardiac acceleration sensor, etc.), would require 33 Mb or 132 Mb of memory with, or without, compression, respectively.

When the memory 208 is filled, such as indicated by status indicator 213, the patient may simply remove peripheral memory patch 200, place the patch into a mailer, and send the peripheral memory patch to the patient's physician or other healthcare provider via regular mail for analysis. Data retrieval for a physician's review may be effected via a direct connection to a computer-based evaluation system using a miniature connector that couples to output device 212. Alternatively, peripheral memory patch 200 may include a transmitter (not shown) for purposes of uplinking data stored in memory 208 to a receiving/storage system using an RF or infrared local area network (LAN) PC port connection.

In an alternative embodiment, peripheral memory patch 200 may be implanted subcutaneously rather than being applied to the patient's outer skin layer. In such an embodiment, the subcutaneous peripheral memory implant may receive telemetry data from an implantable medical device via various receiving and transmitting telemetry techniques. In such a configuration, and with reference to FIG. 3, peripheral memory implant 200 would include a transmitter for purposes of uplinking physiologic and other data received from IMD 216 and stored in memory 208 to an external recording or memory device. Suitable telemetry approaches consistent with this alternative embodiment include the telemetry techniques disclosed in U.S. Pat. No. 4,987,897 and 5,113,859 to Funke, or an RF telemetry approach such as that disclosed in previously referenced U.S. Pat. No. 5,683,432 to Goedeke.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use of a peripheral memory patch in conjunction with a particular implantable medical device, such as a pacemaker, but may be used in conjunction with other medical devices as well. The present invention is also not limited to specific data acquisition and communications techniques, such as those presented herein, but such functions may be directed using other like techniques. The present invention further includes within its scope methods of using a peripheral memory patch as well as the structural particulars described hereinabove.

In the claims, means plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A system for acquiring and storing physiologic data of a patient, comprising:

a body implantable medical device (IMD) that acquires the physiologic data and stores the acquired physiologic data in a memory of said IMD; and a patch apparatus for attachment to a patient's skin, comprising:

a resilient substrate comprising an adhesive for affixing the substrate to the patient's skin;

a receiver device provided on the substrate, the receiver device receiving the physiologic data stored in IMD memory and transmitted by the body implantable medical device;

a processor and a patch memory respectively provided on the substrate, the patch memory storing the received physiologic data and storing patient related information;

a power source provided on the substrate and coupled to at least the processor and the patch memory; and an output device coupled to the processor and the patch memory, the processor coordinating the transfer of the physiologic data from the patch memory to the output device in response to a transfer signal.

2. The system of claim 1, wherein the patch memory comprises a chip-on-board type memory.

3. The system of claim 1, wherein the patch memory comprises dynamic random access memory (DRAM), static random access memory (SRAM), electrically erasable programmable read only memory (EEROM), flash memory, ferroelectric memory, or analog memory.

4. The system of claim 1, wherein the physiologic data is stored in a compressed format in the patch memory.

5. The system of claim 1, wherein the patch memory has a storage capacity sufficient to store the patient's physiologic data acquired on a continuous basis over a period of at least 24 hours.

6. The system of claim 1, wherein the output device comprises a transmitter or a communications interface.

7. The system of claim 1, wherein the output device comprises a radio frequency transmitter or an infrared output port.

8. The system of claim 1, wherein the transfer signal is generated by the processor, the body implantable medical device or a switch actuatable by the patient.

9. The system of claim 1, wherein the transfer signal is generated by the processor in response to a memory storage capacity condition of the IMD memory.

10. The system of claim 1, wherein:
the transfer signal is generated by the processor in response to the IMD memory storing a preestablished amount of physiologic data in a first portion of the IMD memory; and
the implantable medical device transmits the physiologic data stored in first portion of the IMD memory to the receiver of the patch apparatus while storing acquired physiologic data in a second portion of the IMD memory.

11. The system of claim 1, wherein the physiologic data is transferred from the implantable medical device to the receiver device of the patch apparatus using a radio frequency telemetry technique, an acoustic telemetry technique or using the patient's body as a transmission medium.

12. The system of claim 1, wherein the patch apparatus has a thickness of approximately 0.025" to approximately 0.25".

13. The system of claim 1, wherein the implantable medical device comprises one of a pacemaker, a pacemaker/cardioverter/defibrillator (PCD), an oxygen sensing device, a nerve stimulator, a muscle stimulator, or an implantable monitoring device.

14. The system of claim 1, further comprising an input interface coupled to the patch memory and processor, the input interface receiving patient related information from an external information encoding device.

15. A patch apparatus for attachment to a patient's skin system and storing physiologic data of a patient received from a body implantable medical device, the patch apparatus comprising:
a resilient substrate adapted for affixation to the patient;
a receiver device provided on the substrate, the receiver device receiving the physiologic data transmitted by the body implantable medical device;
a processor and a memory respectively provided on the substrate, the memory storing the received physiologic data and storing patient related information;
a power source provided on the substrate and coupled to at least the processor and the memory; and
an output device coupled to the processor and the memory, the processor coordinating the transfer of the physiologic data from the memory to the output device in response to a transfer signal.

16. The apparatus of claim 15, wherein the memory comprises a chip-on-board type memory.

17. The apparatus of claim 15, wherein the memory comprises dynamic random access memory (DRAM), static random access memory (SRAM), electrically erasable programmable read only memory (EEROM), flash memory, ferroelectric memory, or analog memory.

18. The apparatus of claim 15, wherein the physiologic data is stored in a compressed format in the memory.

19. The apparatus of claim 15, wherein the memory has a storage capacity sufficient to store the patient's physiologic data acquired on a continuous basis over a period of at least 24 hours.

20. The apparatus of claim 15, wherein the memory has a storage capacity sufficient to store the patient's physiologic data acquired over at least a 48 hour period.

21. The apparatus of claim 15, wherein the transfer signal is generated by the processor or by the body implantable medical device.

22. The apparatus of claim 15, further comprising a switch, the switch, when actuated by the patient, generating the transfer signal.

23. The apparatus of claim 15, wherein the output device comprises a transmitter or a communications interface.

24. The apparatus of claim 15, wherein the receiver device of the patch apparatus comprises a radio frequency receiver or an acoustic receiver.

25. The apparatus of claim 15, wherein the resilient substrate comprises an interconnect pattern that electrically couples the processor to one or more of the memory, power source, receiver device, and output device, respectively.

26. The apparatus of claim 15, wherein the patch apparatus has a thickness of approximately 0.025" to approximately 0.25".

27. The apparatus of claim 15, wherein the power source comprises a foil type battery.

28. The apparatus of claim 15, wherein the power source comprises a lithium material.

29. The apparatus of claim 15, further comprising a status indicator, the status indicator providing an indication of patch memory storage capacity to the patient.

30. The apparatus of claim 15, further comprising one or more electrodes coupled to the processor and engaging the patient's skin, the electrodes imparting subcutaneous stimulation to the patient as an indication of patch memory storage capacity.

31. The apparatus of claim 15, wherein the substrate is a resilient substrate.

32. The apparatus of claim 15, wherein the substrate is adapted for affixation to the patient's skin or an article of clothing.

33. The apparatus of claim 15, further comprising an input interface coupled to the memory and processor, the input interface receiving patient related information from an external information encoding device.

34. The apparatus of claim 15, further comprising a circuit for activating the patch apparatus for operation upon detecting an impedance change in response to affixing the substrate to the patient.

35. A method of storing physiologic data of a patient acquired by an implantable medical device, comprising:
providing a resilient patch apparatus comprising a memory having patient related information therein, the patch apparatus being adapted for attachment on the patient's skin;
generating a transfer signal; and
transferring, in response to the transfer signal, data stored in the implantable medical device to the memory of the patch apparatus.

36. The method of claim 35, further comprising indicating to the patient a status of storage capacity of the patch apparatus memory.

37. The method of claim 36, wherein indicating the status of memory storage capacity comprises visually, audibly, verbally or tactually indicating the status of memory storage capacity to the patient.

38. The method of claim 35, wherein generating the transfer signal comprises generating the transfer signal by the implantable medical device or by the patch apparatus.

39. The method of claim 35, wherein generating the transfer signal comprises generating the transfer signal in response to patient actuation of a switch of the patch apparatus.

40. The method of claim 35, further comprising transferring the data stored in the memory of the patch apparatus to a memory of a receiving system separate from the patch apparatus.

41. The method of claim 35, further comprising storing physiologic data in the implantable medical device and concurrently transmitting physiologic data previously acquired by the implantable medical device to the memory of the patch apparatus.

42. The method of claim 35, further comprising:
storing physiologic data acquired by the implantable medical device in a first portion of memory provided in the implantable medical device; and
transmitting physiologic data previously acquired by the implantable medical device and stored in a second portion of memory provided in the implantable medical device to the memory of the patch apparatus.

43. The method of claim 35, further comprising:
storing physiologic data acquired by the implantable medical device in a first portion of memory provided in the implantable medical device; and
storing program code received from the patch apparatus in a second portion of memory provided in the implantable medical device.

44. The method of claim 35, wherein transferring the data stored in the implantable medical device to the memory of the patch apparatus comprises transferring the data stored in the implantable medical device to the memory of the patch apparatus using a radio frequency (RF) technique, an acoustic technique or a body bus technique.

45. The method of claim 35, wherein the implantable medical device comprises one of a pacemaker, a pacemaker/cardioverter/defibrillator (PCD), an oxygen sensing device, a nerve stimulator, a muscle stimulator, or an implantable monitoring device.

46. The method of claim 35, further comprising:
operating the patch apparatus in a power savings mode during periods in which no data is transferred from the implantable medical device to the memory of the patch apparatus; and
operating the patch apparatus in an uplink mode of operation in response to the transfer signal.

47. The method of claim 35, further comprising downloading program code for storage in the implantable medical device while transferring substantially all physiologic data acquired by the implantable medical device for storage in the memory of the patch apparatus.

48. The method of claim 35, further comprising activating the patch apparatus for operation upon detecting an impedance change in response to affixing the patch apparatus to the patient.

49. An apparatus for storing physiologic data of a patient acquired by an implantable medical device, comprising:
a patch apparatus adapted for attachment on the patient's skin;
a memory carried on said patch apparatus and storing patient related information;
means for generating a transfer signal; and
means for transferring, in response to the transfer signal, data stored in the implantable medical device to the patch apparatus.

50. The apparatus of claim 49, further comprising means for indicating to the patient a status of storage capacity of the patch apparatus memory.

51. The apparatus of claim 49, wherein the generating means comprises means for generating the transfer signal by the implantable medical device or by the patch apparatus.

52. The apparatus of claim 49, further comprising means for transferring the data stored in the memory of the patch apparatus to a memory of a receiving system separate from the patch apparatus.

53. The apparatus of claim 49, wherein the transferring means comprises means for transferring the data stored in the implantable medical device to the memory of the patch apparatus using a radio frequency (RF) technique, an acoustic technique or a body bus technique.

54. The apparatus of claim 49, wherein the implantable medical device comprises one of a pacemaker, a pacemaker/cardioverter/defibrillator (PCD), an oxygen sensing device, a nerve stimulator, a muscle stimulator, or an implantable monitoring device.

55. The apparatus of claim 49, further comprising means for activating the patch apparatus for operation upon detecting an impedance change in response to affixing the patch apparatus to the patient.

* * * * *